US012586499B2

(12) United States Patent (10) Patent No.: US 12,586,499 B2
Wu et al. (45) Date of Patent: Mar. 24, 2026

(54) DISPLAY DEVICE

(71) Applicant: InnoLux Corporation, Miao-Li County (TW)

(72) Inventors: Yuan-Lin Wu, Miao-Li County (TW); Kuan-Feng Lee, Miao-Li County (TW)

(73) Assignee: InnoLux Corporation, Miao-Li County (TW)

( * ) Notice: Subject to any disclaimer, the term of this patent is extended or adjusted under 35 U.S.C. 154(b) by 0 days.

(21) Appl. No.: 19/045,572

(22) Filed: Feb. 5, 2025

(65) Prior Publication Data

US 2025/0285571 A1 Sep. 11, 2025

(30) Foreign Application Priority Data

Mar. 11, 2024 (CN) .......................... 202410271430.0

(51) Int. Cl.
 *G09G 3/00* (2006.01)
 *A61B 5/00* (2006.01)
 *H10K 59/121* (2023.01)
(52) U.S. Cl.
 CPC .............. *G09G 3/03* (2020.08); *A61B 5/681* (2013.01); *A61B 5/6898* (2013.01); *H10K 59/121* (2023.02); *G09G 2340/0435* (2013.01)
(58) Field of Classification Search
 None
 See application file for complete search history.

(56) References Cited

U.S. PATENT DOCUMENTS

| | | | | |
|---|---|---|---|---|
| 2008/0146285 A1* | 6/2008 | Lee | ...................... | H04M 1/0279 |
| | | | | 455/566 |
| 2013/0334543 A1* | 12/2013 | Kim | ................... | G02F 1/13454 |
| | | | | 257/79 |
| 2016/0062600 A1* | 3/2016 | Kim | ...................... | G06F 3/0488 |
| | | | | 715/765 |
| 2017/0046109 A1* | 2/2017 | Jung | ...................... | A61B 5/1118 |
| 2021/0304704 A1* | 9/2021 | Wu | .......................... | G09G 5/14 |
| 2021/0376038 A1* | 12/2021 | Won | ................... | H10K 59/1213 |
| 2022/0036810 A1* | 2/2022 | Gu | ............................ | G06T 7/11 |
| 2022/0069051 A1 | 3/2022 | Lee | | |
| 2022/0147104 A1* | 5/2022 | Cho | ...................... | G06F 1/1666 |
| 2022/0189408 A1* | 6/2022 | Jo | ......................... | G09G 3/3275 |
| 2023/0237953 A1* | 7/2023 | Tian | ................... | G09G 3/3233 |
| | | | | 345/55 |
| 2023/0273640 A1 | 8/2023 | Kwak | | |

* cited by examiner

*Primary Examiner* — Nicholas J Lee
(74) *Attorney, Agent, or Firm* — Winston Hsu

(57) ABSTRACT

A display device capable of operating in a plurality of conditions of use is disclosed. The display device includes a display panel and a processor. The display panel has a first area and a second area surrounding the first area, and the second area has a plurality of curve areas and a corner area connecting two of the curve areas. The processor is electrically connected to the display panel, and the processor is configured to: based on one of the conditions of use, determine operation modes corresponding to the first area, the curve areas and the corner area; and control the first area, the curve areas and the corner area to operate in the determined operation modes respectively.

10 Claims, 18 Drawing Sheets

DISPLAY DEVICE

BACKGROUND OF THE DISCLOSURE

1. Field of the Disclosure

The present disclosure relates to a display device, and more particularly to a display device capable of operating in a plurality of conditions of use.

2. Description of the Prior Art

In recent years, display devices have become more and more important in various electronic applications. With a flourishing development of the technology of electronic products, curved electronic devices have become one of the focuses of the new generation electronic technology. However, the conventional display that is bent to have a curved surface has the problem of high power consumption, and it is still necessary for the industry to continue research and development so that non-flat displays can provide more diversified functions.

SUMMARY OF THE DISCLOSURE

One of objectives of the present disclosure is to provide a display device, wherein each area of the display panel operates in a corresponding operation mode based on a condition of use of the display device, so that the effect of power saving may be achieved, and various kinds of divisional display statuses may satisfy different requirements of use.

The present disclosure provides a display device, which is capable of operating in a plurality of conditions of use. The display device includes a display panel and a processor. The display panel has a first area and a second area surrounding the first area, and the second area has a plurality of curve areas and a corner area connecting two of the curve areas. The processor is electrically connected to the display panel, and the processor is configured to: based on one of the conditions of use, determine operation modes corresponding to the first area, the curve areas and the corner area; and control the first area, the curve areas and the corner area to operate in the determined operation modes respectively.

These and other objectives of the present disclosure will no doubt become obvious to those of ordinary skill in the art after reading the following detailed description of the embodiment that is illustrated in the various figures and drawings.

DETAILED DESCRIPTION

Figure 1:
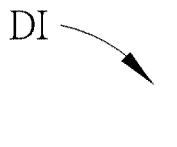
FIG. 1 is a top-view schematic diagram of a display device according to an embodiment of the present disclosure.
Figure 1:
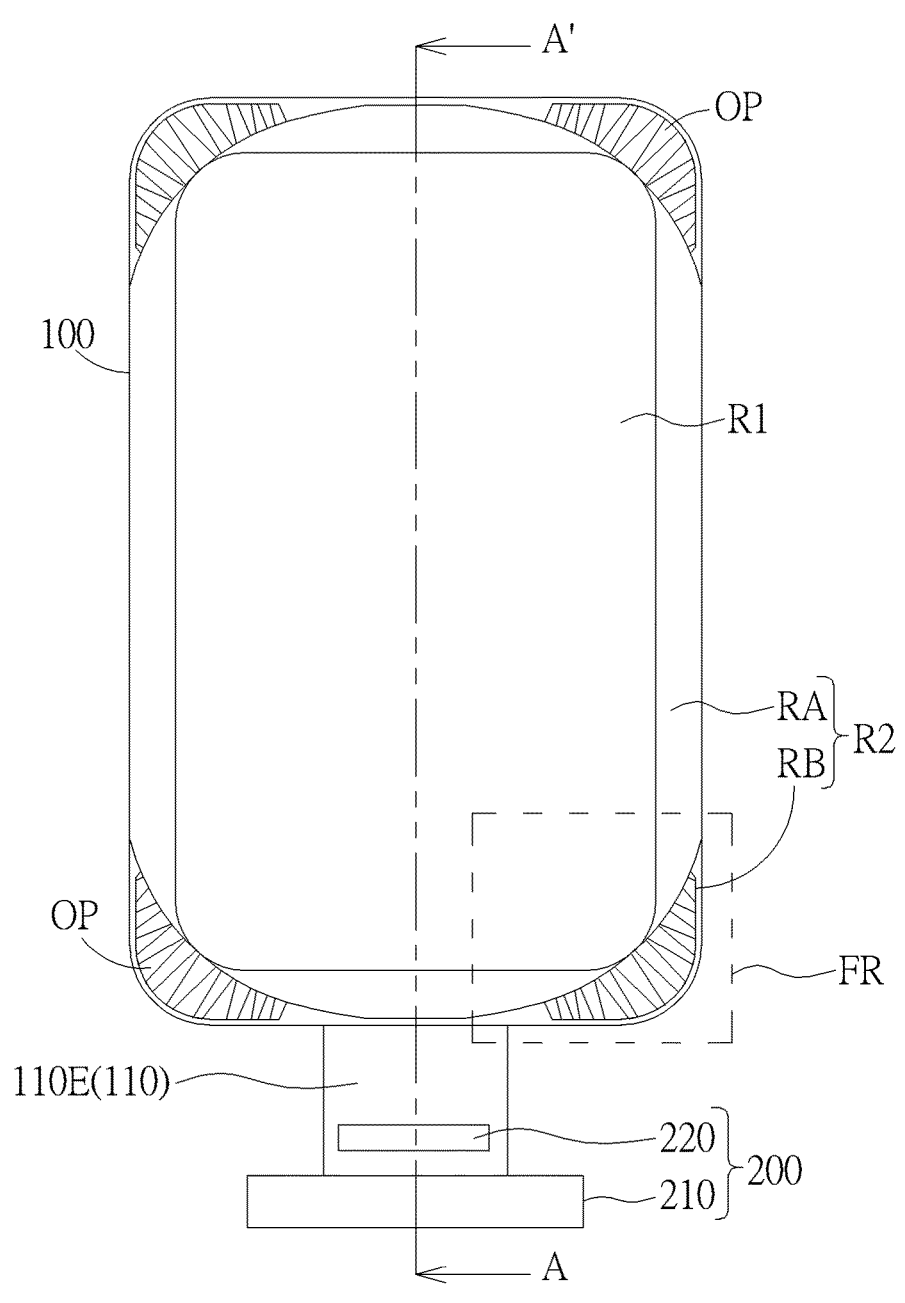

The present disclosure may be understood by reference to the following detailed description, taken in conjunction with the drawings as described below. It is noted that, for purposes of illustrative clarity and being easily understood by the readers, various drawings of this disclosure show a portion of the device or structure, and certain components in various drawings may not be drawn to scale. In addition, the number and dimension of each component shown in drawings are only illustrative and are not intended to limit the scope of the present disclosure.

Certain terms are used throughout the description and following claims to refer to particular components. As one skilled in the art will understand, electronic equipment manufacturers may refer to a component by different names. This document does not intend to distinguish between components that differ in name but not function. In the following description and in the claims, the terms "include", "comprise" and "have" are used in an open-ended fashion, and thus should be interpreted to mean "include, but not limited to . . . ". When the terms "include", "comprise" and/or "have" are used in the description of the present disclosure, the corresponding features, areas, steps, operations and/or components would be pointed to existence, but not limited to the existence or addition of one or a plurality of the corresponding or other features, areas, steps, operations, components and/or combinations thereof.

When an element or layer is referred to as being "on" or "connected to" another element or layer, it may be directly on or directly connected to the other element or layer, or intervening elements or layers may be presented (indirect condition). In contrast, when an element is referred to as being "directly on" or "directly connected to" another element or layer, there are no intervening elements or layers presented.

The directional terms mentioned in this document, such as "up", "down", "front", "back", "left", "right", etc., are only directions referring to the drawings. Therefore, the directional terms used are for illustration, not for limitation of the present disclosure.

The terms "about", "equal", "identical" or "the same", and "substantially" or "approximately" mentioned in this document generally mean being within 20% of a given value or range, or being within 10%, 5%, 3%, 2%, 1% or 0.5% of a given value or range.

The ordinal numbers used in the description and claims, such as "first", "second", "third", etc., are used to describe elements, but they do not mean and represent that the element(s) have any previous ordinal numbers, nor do they represent the order of one element and another element, or the order of manufacturing methods. The ordinal numbers are used only to clearly discriminate an element with a certain name from another element with the same name. The claims and the description may not use the same terms. Accordingly, in the following description, a first constituent element may be a second constituent element in a claim.

The display device of the present disclosure may be applied in an electronic device, wherein the display device may include a non-self-emissive display device or a self-emissive display device. In addition, the electronic device may further include a backlight device, an antenna device, a sensing device or a tiled device, but not limited herein. The electronic device may include a bendable or flexible electronic device. The antenna device may include a liquid-crystal type antenna device or an antenna device other than liquid-crystal type, and the sensing device may include a sensing device used for sensing capacitance, light, heat or ultrasonic waves, but not limited herein. The electronic device may include electronic elements such as passive elements and active elements, for example, capacitors, resistors, inductors, diodes, transistors, etc. The diode may include a light-emitting diode or a photodiode. For example, the light-emitting diode may include an organic light-emitting diode (OLED), a mini light-emitting diode (mini LED), a micro light-emitting diode (micro LED) or a quantum dot light-emitting diode (quantum dot LED), but not limited herein. The tiled device may be, for example, a display tiled device or an antenna tiled device, but not limited herein. It should be noted that the electronic device may be any arrangement and combination of the above, but not limited herein.

It should be noted that the technical features in different embodiments described in the following can be replaced, recombined, or mixed with one another to constitute another embodiment without departing from the spirit of the present disclosure.

Figure 2:
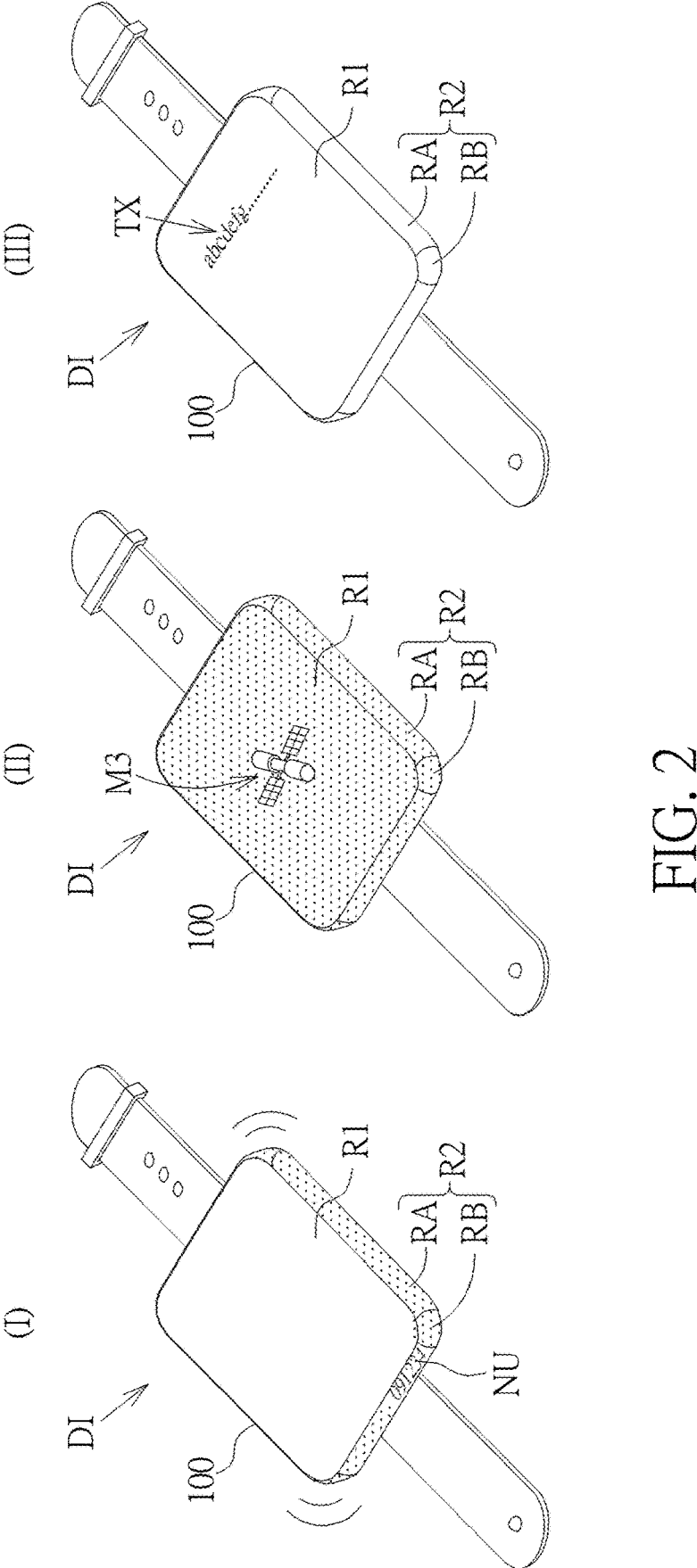
FIG. 2 is an appearance schematic diagram of a display device in different conditions of use according to an embodiment of the present disclosure.
Figure 3:
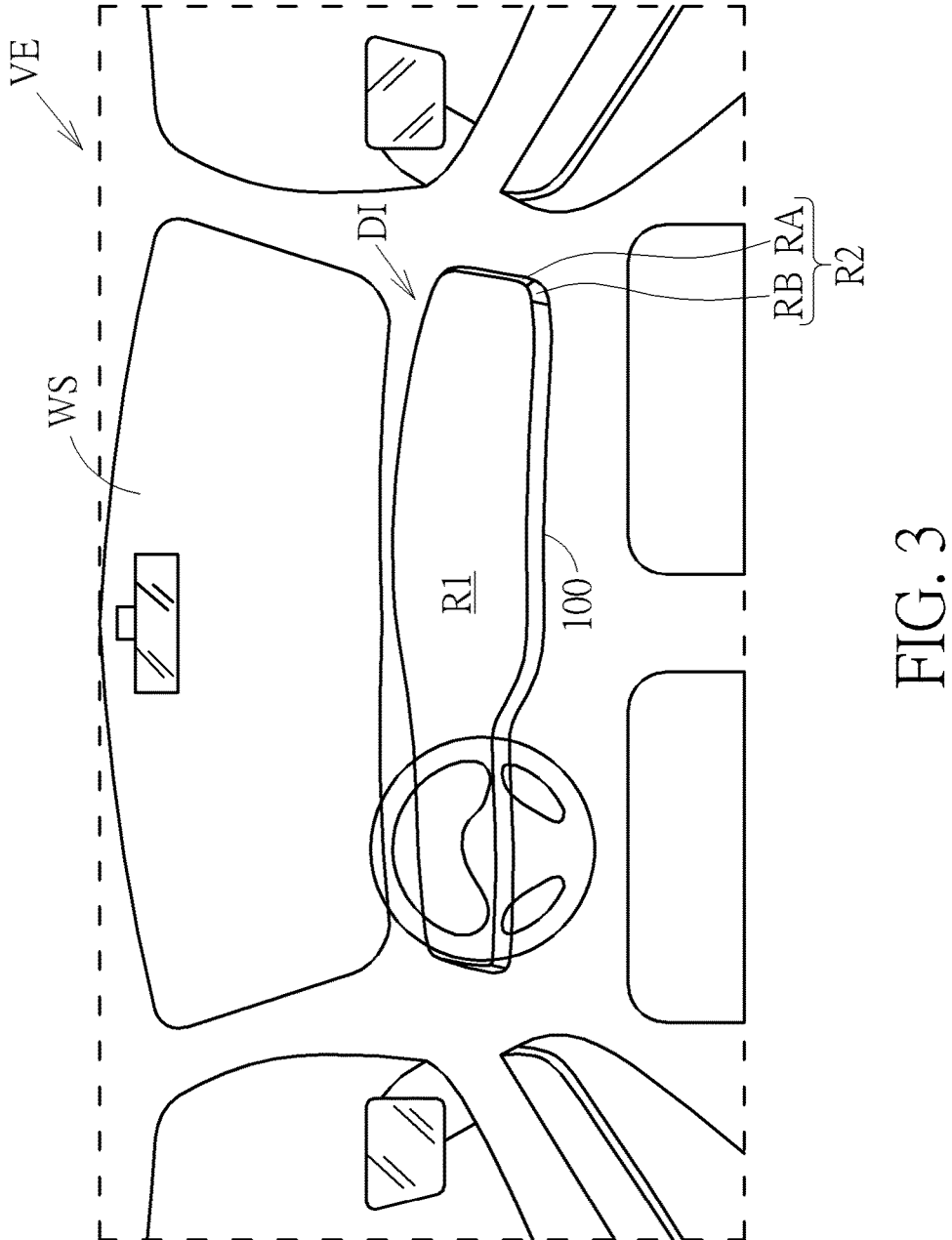
FIG. 3 is a schematic diagram of a display device installed in a vehicle according to another embodiment of the present disclosure.

Please refer to FIG. 1 and FIG. 2. FIG. 1 is a top-view schematic diagram of a display device according to an embodiment of the present disclosure. FIG. 2 is an appearance schematic diagram of a display device in different conditions of use according to an embodiment of the present disclosure. As shown in FIG. 1 and FIG. 2, a display device DI includes a display panel 100 and a processor 200, and the display device DI is capable of operating in a plurality of conditions of use, wherein the conditions of use includes, for example (but not limited to), a first condition of use I, a second condition of use II and a third condition of use III shown in FIG. 2. For example, the display device DI may be a wearable device (as shown in FIG. 2) or a vehicle display (as shown in FIG. 3), or the display device DI may be applied in other suitable electronic devices, such as (but not limited to) a smart phone, a tablet computer, a e-book reader, etc. The display panel 100 has a first area R1 and a second area R2, wherein the second area R2 surrounds the first area R1. The second area R2 has a plurality of curve areas RA and a corner area RB, and the corner area RB connects two of the curve areas RA. The curve area RA may be a one-orientation curved surface with zero Gaussian curvature, while the corner area RB may be a two-orientation curved surface with non-zero Gaussian curvature. The display surfaces of the curve area RA and the corner area RB are not parallel to the display surface of the first area R1. According to the embodiments shown in FIG. 1 and FIG. 2, the second area R2 may include, for example, four curve areas RA and four corner areas RB. The four curve areas RA adjoin four sides of the first area R1 respectively, the four corner areas RB adjoin four corners of the first area R1 respectively, and each of the corner areas RB is located between and connected to two adjacent curve areas RA, wherein the curve areas RA may be regarded as a side wall area connected to the first area R1, and the corner areas RB may be regarded as turning areas connected between the side walls adjacently. However, the number of various area of the display panel 100 of the present disclosure is not limited to the above, and in other embodiments, the number of each area may have various designs according to the products in practice. Taking the embodiment shown in FIG. 3 as an example, wherein FIG. 3 is a schematic diagram of a display device installed in a vehicle according to another embodiment of the present disclosure, the display device DI may be installed on a vehicle VE, such as installed on an instrument panel, a center console and/or a storage compartment (or a glove box) which are below a windshield WS or installed on any suitable device of the vehicle VE, and the display panel 100 of the display device DI may be polygonal or irregular in shape and has a plurality of curve areas RA adjoining a plurality of sides of the first area R1, but not limited herein.

The processor 200 is electrically connected to the display panel 100. The processor 200 may include, for example (but not limited to), a control unit, an integrated circuit chip or a micro integrated circuit (micro IC). According to the embodiment shown in FIG. 1, the processor 200 may include a circuit board 210 and a chip 220, which are electrically connected to the display panel 100. The processor 200 is configured to: based on one of the conditions of use, determine operation modes corresponding to the first area R1, the curve areas RA and the corner area RB; and control the first area R1, the curve areas RA and the corner area RB to be operated in the determined operation modes respectively. The conditions of use may include the first condition of use I, the second condition of use II and/or the third condition of use III, and the operation modes may be a display mode or an off-mode. That is to say, the processor 200 may control every area of the display panel 100 to execute the corresponding operation mode according to different conditions of use, and may make the first area R1, the curve areas RA and the corner areas RB have the same display change rate or different display change rates with each other. Each condition of use of the display device DI and the corresponding operation modes of every area will be further described in detail later.

The term "display change rate" referred in the present disclosure may include the visual image change rate and the driving refresh rate. The visual image change rate is the change in the display image visible to eyes, including brightness change, gray level change and color change. For example, the display image may be changed by providing different data signals. The driving refresh rate is the gate driving frequency of the area, which means the number of frame refreshed per second, such as (but not limited to) 60 Hz, 120 Hz, etc. In some embodiments, the variation range of the refresh rate of the first area R1 may be greater than that of the second area R2. For example, the refresh rate of the first area R1 may range from 1 Hz to 120 Hz, and the refresh rate of the second area R2 may range from 1 Hz to 60 Hz, but not limited herein.

The term "display mode" referred in the present disclosure means a status capable of displaying any gray level, and the display mode may include a high-frequency display mode and a low-frequency display mode. The low-frequency display mode means, for example (but not limited to), providing a gray level signal that can be perceived by human eyes. The "off-mode" referred in the present disclosure may mean a status which is providing a low gray level signal that cannot be perceived by human eyes, providing a zero gray level signal but the refresh rate is not zero, providing no signal, low refresh rate, zero refresh rate or turning off the touch function, etc., wherein the low gray level signal may mean, for example (but not limited to), that the set gray level is less than or equal to one eighth of the total gray level. In the condition of the same area and time, the energy consumption of the off-mode is lower than that of the display mode.

Based on the first condition of use I, the first area R1 may be operated in the off-mode or the display mode, and the curve areas RA and the corner area RB are operated in the display mode. The first condition of use I includes, for example, a condition that the display device DI is operated in a call reminder mode, a charging mode, a sensing mode, a music mode and/or a running mode, but not limited herein. Specifically, take the first condition of use I shown in FIG. 2 as an example, which shows that the first condition of use I is the condition that the display device DI is operated in the call reminder mode. As shown in FIG. 2, in the first condition of use I, the first area R1 may be operated in the off-mode, and the curve areas RA and the corner areas RB surrounding the first area R1 may be operated in the display mode to show colors (indicated by the shading). In some embodiments, the curve areas RA and the corner areas RB may show various colors in a blinking manner, so that the color shown by the curve areas RA are the same as or different from the color shown by the corner areas RB, wherein the displayed colors may be adjusted to various colors by a user, for example.

According to the embodiment shown in FIG. 2, in the first condition of use I, the curve area RA may further show the incoming call number NU in a marquee scroll manner, such as sequentially displaying the numbers of the incoming call number NU in one of the curve areas RA in the marquee scroll manner. For example, the incoming call number NU may be "0912345678", and the first condition of use I in FIG. 2 shows the status that the incoming call number NU is shown till "091234" in the curve area RA during the marquee scroll display process, while the curved areas RA may further show the incoming call number NU in the marquee scroll manner surrounding the first area R1. In some embodiments, one of the curve areas RA may further show a calling icon. In other embodiments, the first area R1 may be operated in the display mode at the same time to show the calling icon, and the curve areas RA and the corner areas RB surrounding the first area R1 may show different colors according to different callers. For example, the user may preset the display device DI, so that the curve areas RA and the corner areas RB show different colors respectively in the condition of family calls, colleague calls and unknown calls.

According to the above various types of call reminder, in the first condition of use I, since the first area R1 is in the off-mode or only shows the calling icon and the second area R2 needs to show the call reminder, the display change rate of the second area R2 is greater than the display change rate of the first area R1. Specifically, the refresh rate of the curve area RA may be greater than the refresh rate of the first area R1, and the refresh rate of the corner area RB may be greater than the refresh rate of the first area R1. For example, the refresh rate of the first area R1 may be 1 Hz, and the refresh rate of the curve area RA and/or the corner area RB may be 30 Hz, but not limited herein.

Figure 4:
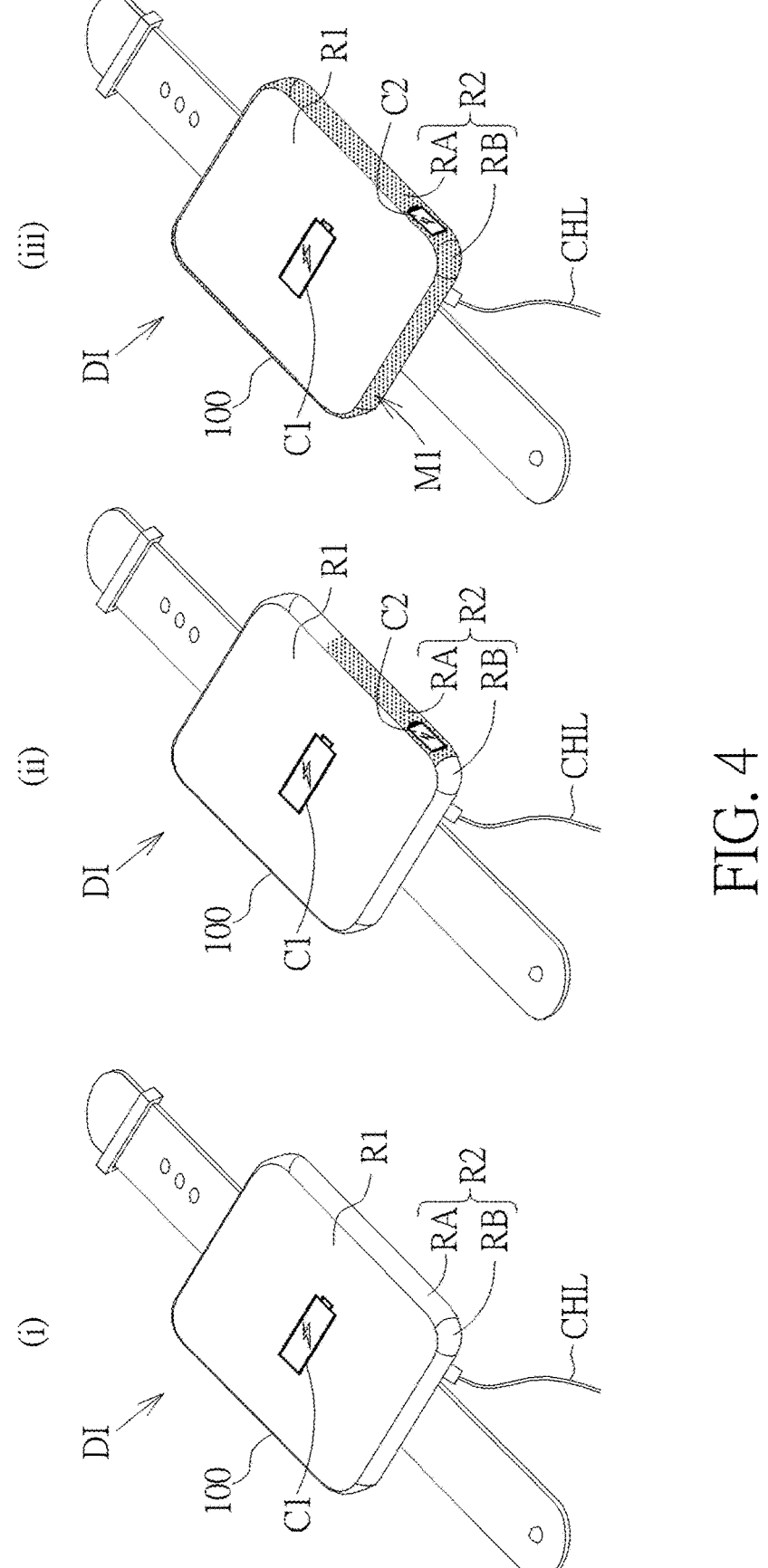
FIG. 4 is an appearance schematic diagram of an embodiment of a display device in a first condition of use according to the present disclosure.

Please refer to FIG. 4, which is an appearance schematic diagram of an embodiment of a display device in a first condition of use according to the present disclosure. The first condition of use I in this embodiment is the condition that the display device DI is operated in a charging mode. According to the embodiment shown in FIG. 4, the first area R1 may be operated in the display mode to show a charging icon C1 or operated in the off-mode without showing any icon, and the curve areas RA and the corner areas RB surrounding the first area R1 may be operated in the display mode to indicate completeness of a task, wherein the above task in this embodiment may refer to charging a battery of the display device DI, such as (but not limited to) charging the battery of the display device DI through a charging line CHL. The status (i), status (ii) and status (iii) shown in FIG. 4 respectively indicate different completeness of charging of the display device DI. As shown in the status (i) of FIG. 4, when the completeness of charging of the display device DI is 0%, the first area R1 shows the charging icon C1. As shown in the state (ii) of FIG. 4, when the completeness of charging of the display device DI is greater than 0% and less than 100%, a portion of the curve areas RA and/or the corner area RB correspondingly shows color (marked by the shading) according to the current completeness of charging, and the curve area RA may further show a charging icon C2 at this time. As shown in the status (iii) of FIG. 4, when the completeness of charging of the display device DI is 100%, the curve areas RA and the corner areas RB of the entire second area R2 all display the color to indicate the charging is complete. That is to say, the completeness of charging of a specific task (such as charging or sensing) may be presented by the degree to which the color shown in the second area R2 surrounds the first area R1. When the task is complete, the curve areas RA and the corner areas RB show an image M1 surrounding the first area R1. According to the various types of charging described above, in the first condition of use I, since the first area R1 only shows the charging icon C1 or is in the off-mode while the second area R2 needs to show the completeness of charging, the display change rate of the second area R2 is greater than the display change rate of the first area R1.

Figure 5:
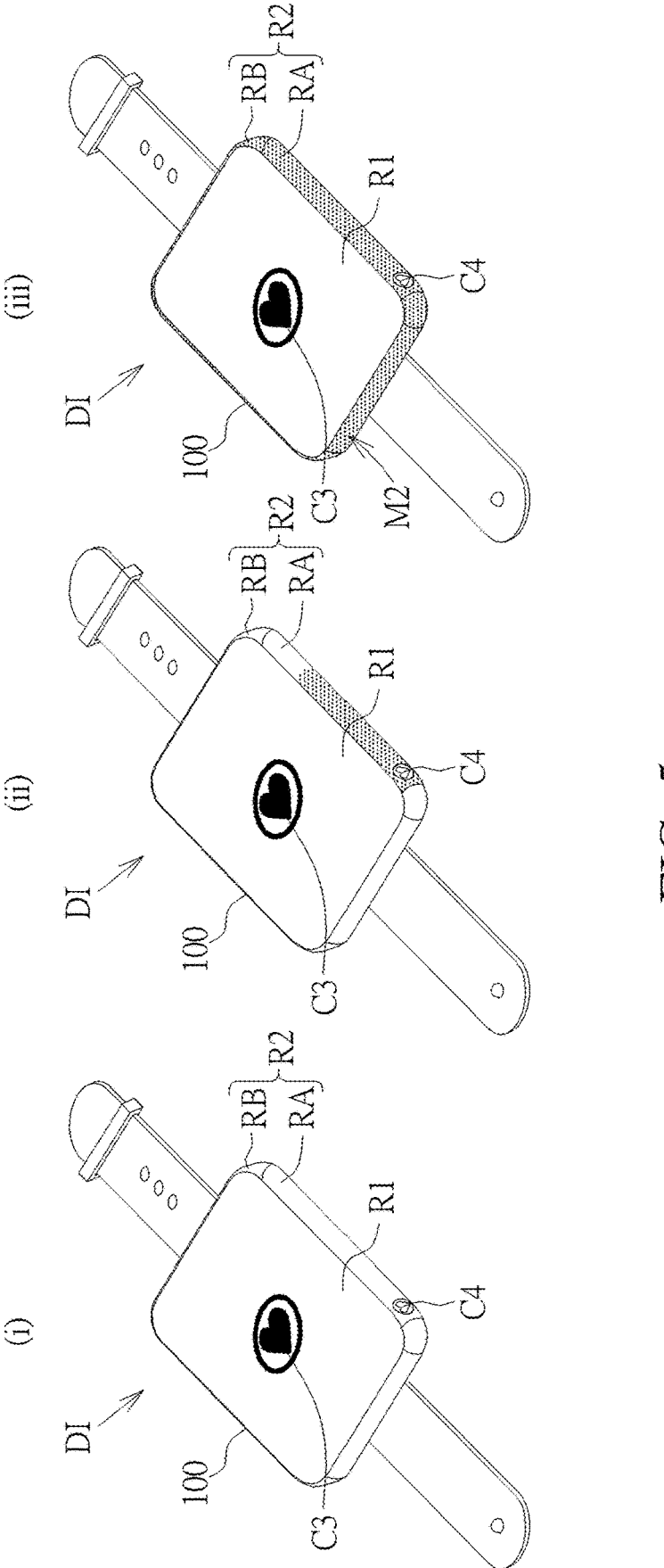
FIG. 5 is an appearance schematic diagram of another embodiment of a display device in a first condition of use according to the present disclosure.

Please refer to FIG. 5, which is an appearance schematic diagram of another embodiment of a display device in a first condition of use according to the present disclosure. The first condition of use I in this embodiment is the condition that the display device DI is operated in a sensing mode. According to the embodiment shown in FIG. 5, the first area R1 may be operated in the display mode to show a sensing icon C3 or operated in the off-mode without showing any icon, and the curve areas RA and the corner areas RB surrounding the first area R1 may be operated in the display mode to indicate completeness of a task, wherein the above task in this embodiment may refer to sensing a physiological status of a user, and the physiological status may be one of heart rate, blood pressure and blood oxygen level, for example. The status (i), status (ii) and status (iii) shown in FIG. 5 respectively indicate different completeness of sensing the physiological status. As shown in the status (i) of FIG. 5, when the completeness of sensing of the display device DI is 0%, the first area R1 shows the sensing icon C3, and the curve area RA may further shown another sensing icon C4. As shown in the state (ii) of FIG. 5, when the completeness of sensing of the display device DI is greater than 0% and less than 100%, a portion of the curve areas RA and/or the corner area RB shows color (marked by the shading) according to the current completeness of sensing. As shown in the status (iii) of FIG. 5, when the completeness of sensing of the display device DI is 100%, the curve areas RA and the corner areas RB of the entire second area R2 all display the color to indicate the sensing is complete. That is to say, when the sensing is complete, the curve areas RA and the corner areas RB show an image M2 surrounding the first area R1. According to the various types of sensing described above, in the first condition of use I, since the first area R1 only shows the sensing icon C3 or is in the off-mode while the second area R2 needs to show the completeness of sensing, the display change rate of the second area R2 is greater than the display change rate of the first area R1.

In some embodiments, when the first condition of use I is the condition that the display device DI is operated in a music mode (not shown), the curve areas RA and the corner areas RB of the second area R2 may show one or more colors as an atmosphere light. The atmosphere light may further flash or the color thereof may be changed along with the rhythm of the music, and the first area R1 may be operated in the off-mode or operated in the display mode to show pictures. In other embodiments, when the first condition of use I is the condition that the display device DI is operated in the running mode (not shown), the curve areas RA and the corner areas RB of the second area R2 may show color as a warning light, wherein the user may be more conspicuous with the warning light when exercising at night, and the first area R1 may be in the off-mode.

Please refer to FIG. 2. Based on the second condition of use II, the first area R1, the curve areas RA and the corner areas RB are operated in the display mode to show at least one image M3. The second condition of use II includes, for example (but not limited to), a condition that the display device DI is operated in a picture mode. The first area R1 and the second area R2 show an image in common, so that the displayed image provide a unity sense, and the visual affection of the border may be reduced, thereby improving the display quality. In the second condition of use II, since both the first area R1 and the second area R2 are used to show the image M3, wherein the two areas need to have the same display quality, the display change rate of the second area R2 is equal to or less than the display change rate of the first area R1. Specifically, the refresh rate of the curve area RA is equal to the refresh rate of the first area R1, and the refresh rate of the corner area RB is equal to the refresh rate of the first area R1. In some embodiments, the first area R1 may show the main portion of the image, and the corner area RB may display the secondary portion or background of the image. At this time, the refresh rate of the corner area RB may be lower than the refresh rate of the first area R1. For example, the refresh rate of the first area R1 may be 120 Hz, and the refresh rate of the corner area RB may be 60 Hz, but not limited herein.

Based on the third condition of use III shown in FIG. 2, the curve areas RA and the corner areas RB are operated in the off-mode, and the first area R1 is operated in the display mode to show a context TX. The third condition of use III includes, for example (but not limited to), the condition that the display device DI is operated in a reading mode. It is inconvenient for the user to read the text shown in the curve areas RA and the corner areas RB, so only the first area R1 show the context TX. In the third condition of use III, since the display quality of the first area R1 is required to be higher, the display change rate of the first area R1 is greater than the display change rate of the second area R2. Specifically, the refresh rate of the first area R1 may be greater than the refresh rate of the curve area RA, and the refresh rate of the first area R1 may be greater than the refresh rate of the corner area RB. For example, the refresh rate of the first area R1 may be 60 Hz, and the refresh rate of the corner area RB may be 1 Hz, but not limited herein.

According to the various embodiments of the present disclosure described above, the processor 200 may control the first area R1, the curve areas RA and the corner areas RB to operate in the display mode or the off-mode respectively based on the first condition of use I, the second condition of use II or the third condition of use III, so that the first area R1, the curve areas RA and the corner areas RB have the same display change rate or different display change rates with each other, thereby achieving the effect of power saving, and various kinds of divisional display statuses may satisfy different requirements of use.

Figure 6A:
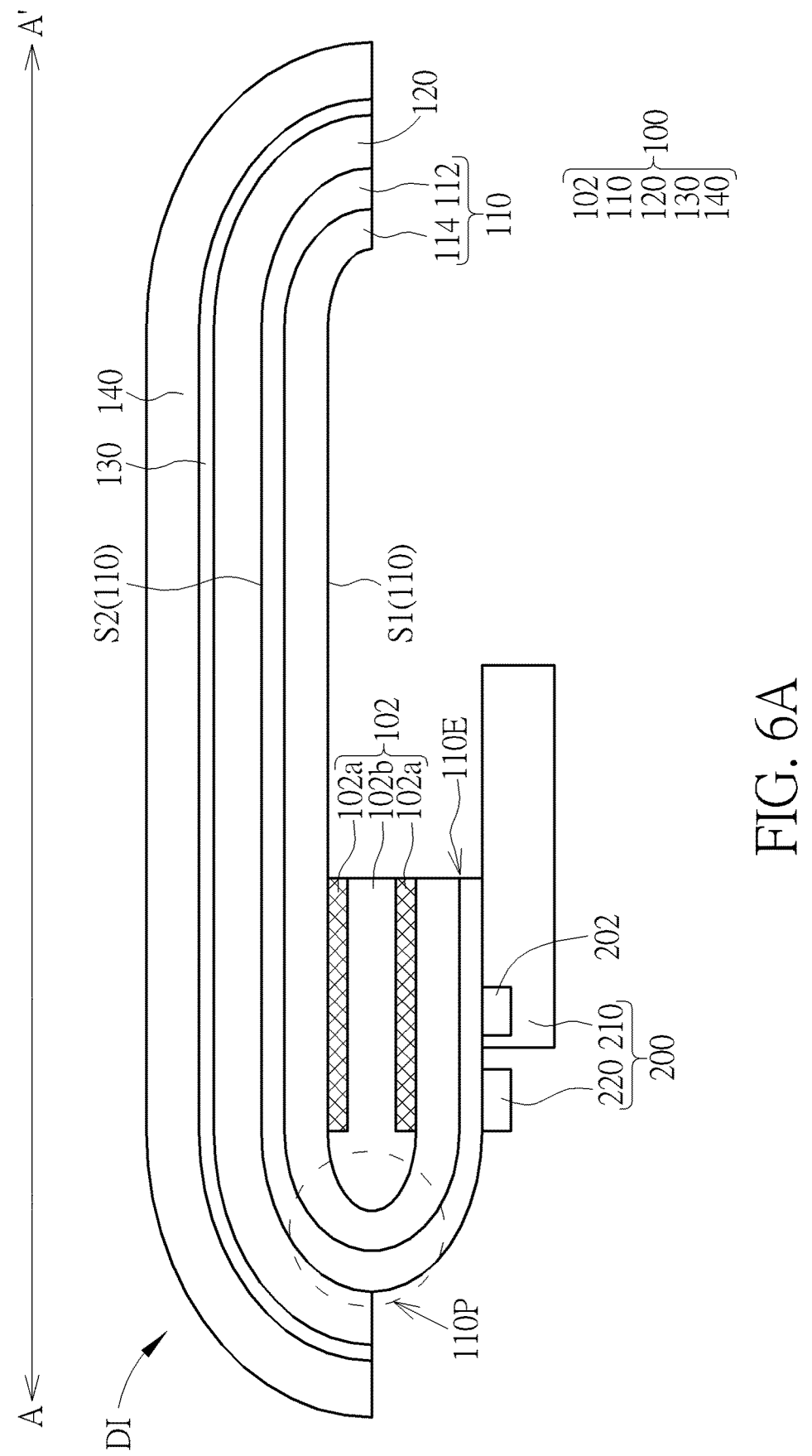
FIG. 6A to FIG. 6C are partial cross-sectional schematic diagrams of some embodiments of a display device according the present disclosure.
Figure 6B:
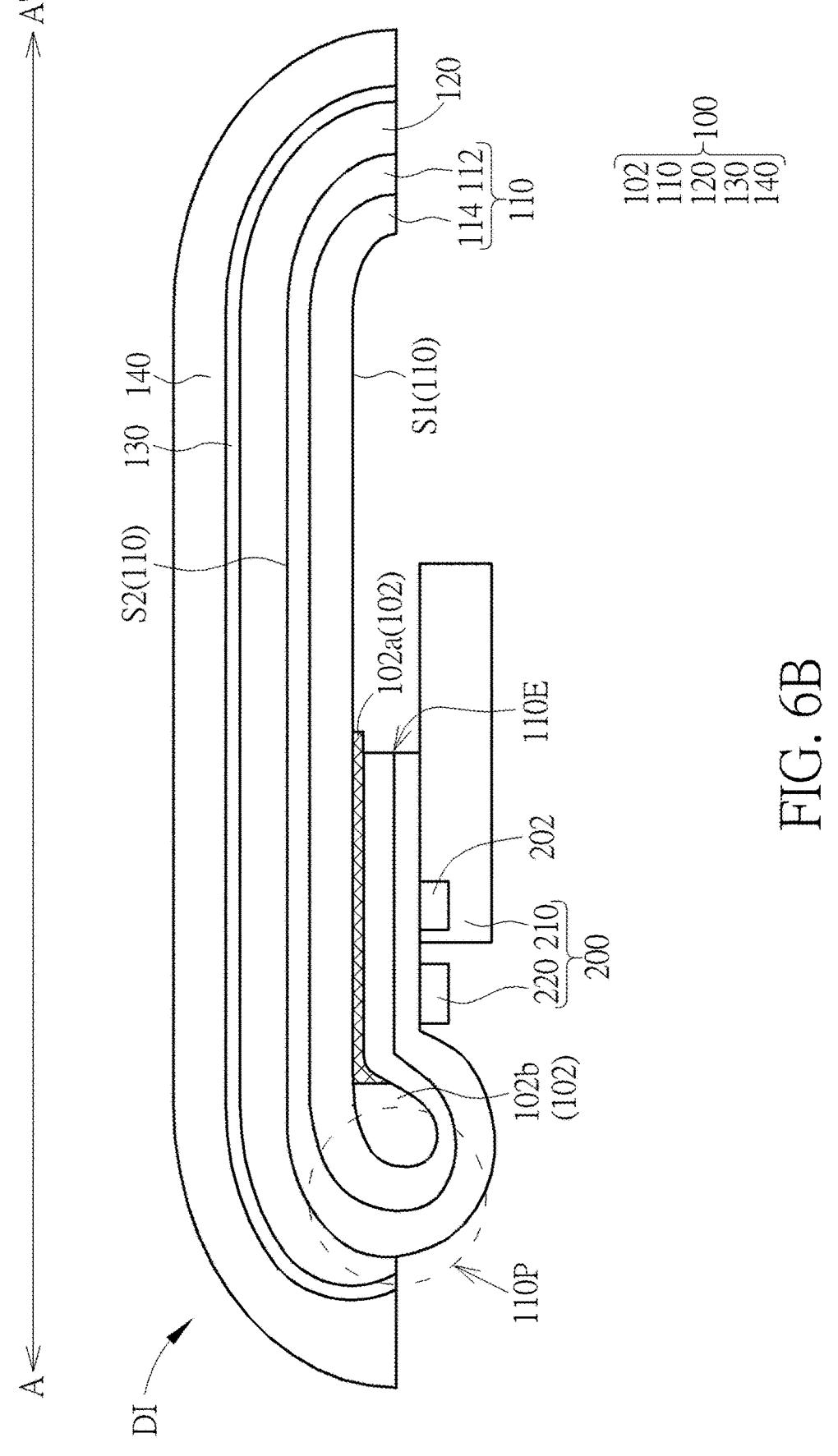
Figure 6C:
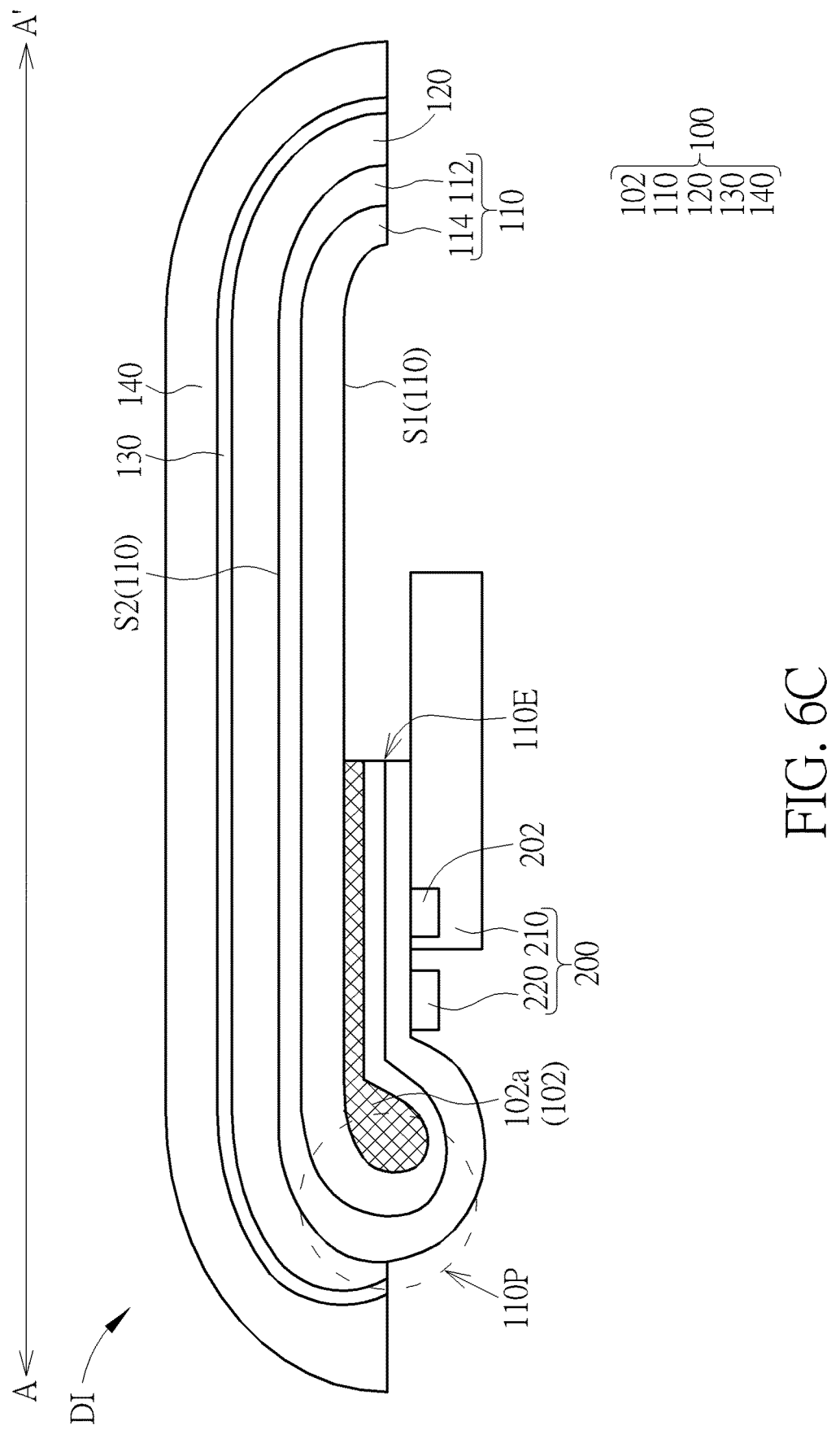

Please refer to FIG. 6A to FIG. 6C, in conjunction with FIG. 1. FIG. 6A to FIG. 6C are partial cross-sectional schematic diagrams of some embodiments of a display device according the present disclosure, which respectively show the corresponding detail relationship of each layer of a display device according to some embodiments of the present disclosure. When an end portion 110E of a substrate 110 of the display device DI shown in FIG. 1 is bent to a back side S1, a portion of the cross-sectional structure obtained along the section line A-A' may refer to the embodiment shown in FIG. 6A, FIG. 6B or FIG. 6C. As shown in FIG. 6A to FIG. 6C and FIG. 1, the display panel 100 includes the substrate 110 that is flexible, and the substrate 110 may include a base layer 112 and a supporting layer 114. The base layer 112 is disposed on the supporting layer 114. The processor 200 may include a circuit board 210 and a chip 220 disposed on the end portion 110E of the substrate 110. The circuit board 210 may be electrically connected to the display panel 100 through a connection pad 202 disposed on the end portion 110E, for example. In the corner areas RB, the substrate 110 may further have a plurality of openings OP (shown in FIG. 1) to facilitate the bending of the corner areas RB. The materials of the base layer 112 and the supporting layer 114 include, for example, polyimide (PI), polycarbonate (PC), polyethylene terephthalate (PET) or poly (methyl methacrylate) (PMMA), but not limited herein.

As shown in FIG. 6A to FIG. 6C, the end portion 110E together with the circuit board 210 and the chip 220 disposed thereon may be bent to the back side S1 of the substrate 110. Specifically, the display panel 100 may include a supporting structure 102, and the supporting structure 102 may be disposed between the end portion 110E of the substrate 110 bent to the back side S1 and the non-bending portion of the substrate 110, so as to reduce the break probability of the bending portion of the display panel 100. The display panel 100 may further include a display layer 120, an adhesive layer 130 and a cover layer 140. The display layer 120 is disposed on a front side S2 of the substrate 110, the adhesive layer 130 is disposed on the display layer 120, and the cover layer 140 is disposed on the adhesive layer and connected to the display layer 120 through the adhesive layer 130.

According to the embodiment shown in FIG. 6A, the supporting structure 102 may include an adhesive layer 102a and a supporting portion 102b, and the adhesive layer 102a is located at two opposite sides (e.g., upper and lower sides) of the supporting portion 102b, so that the end portion 110E and the non-bending portion of the substrate 110 may be respectively attached to the two sides of the supporting portion 102b through the adhesive layers 102a, wherein the supporting portion 102b may contact a bending portion 110P of the substrate 110. According to the embodiment shown in FIG. 6B, the supporting structure 102 may include an adhesive layer 102a and a supporting portion 102b, and the end portion 110E and the non-bending portion of the substrate 110 may be attached to each other through the adhesive layer 102a, wherein the supporting portion 102b is located at one side of the adhesive layer 102a and closer to the bending portion 110P of the substrate 110 than the adhesive layer 102a, and the supporting portion 102b may contact the bending portion 110P of the substrate 110. According to the embodiment shown in FIG. 6C, the supporting structure 102 may include only the adhesive layer 102a. Through the above designs of the supporting structure 102, the break probability of the bending portion of the display panel 100 may be reduced.

Figure 7:
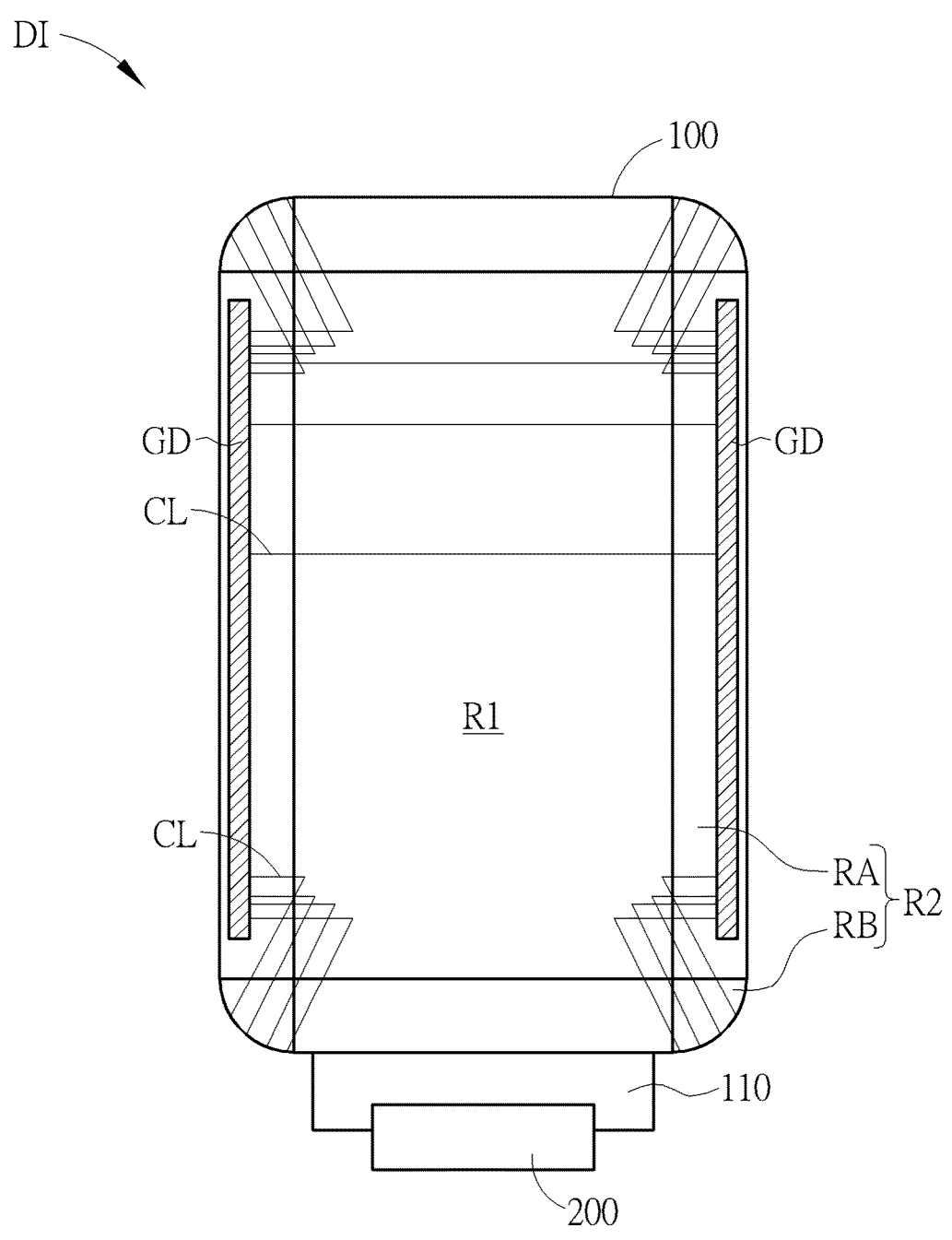
FIG. 7 is a top-view schematic diagram of the architecture of a first embodiment of a display device according the present disclosure.

Please refer to FIG. 7, which is a top-view schematic diagram of the architecture of a first embodiment of a display device according the present disclosure. According to the display device DI shown in FIG. 7, the display panel 100 may include a gate driver GD disposed in at least one of the curve areas RA, and the gate driver GD is configured to provide a plurality of scan signals to the first area R1 and the second area R2. As shown in FIG. 7, the display panel 100 may include a plurality of wires CL (such as scan lines). In order to simplify the drawing, FIG. 7 only shows a portion of the wires CL for illustration, and similar simplified drawings are also depicted in other top views in the following, which will not be redundantly described. The gate driver GD is electrically connected to each wire CL and the processor 200, and the gate driver GD may provide a plurality of scan signals to the first area R1, the curve areas RA and the corner areas RB through the wires CL respectively. The gate driver GD is, for example (but not limited to), a gate driver on panel (GOP), which may be disposed in a peripheral area (or referred to as a non-display area) of the curve area RA. The first area R1, the curve area RA and the corner area RB may respectively have a display area and a peripheral area, and the peripheral area may be located at one side of the display area and close to the edge of the display panel 100. In some embodiments, the display panel 100 may include two gate drivers GD, which are respectively disposed in two curve areas RA located at two opposite sides (e.g., left and right sides) of the first area R1, but not limited herein.

Figure 8:
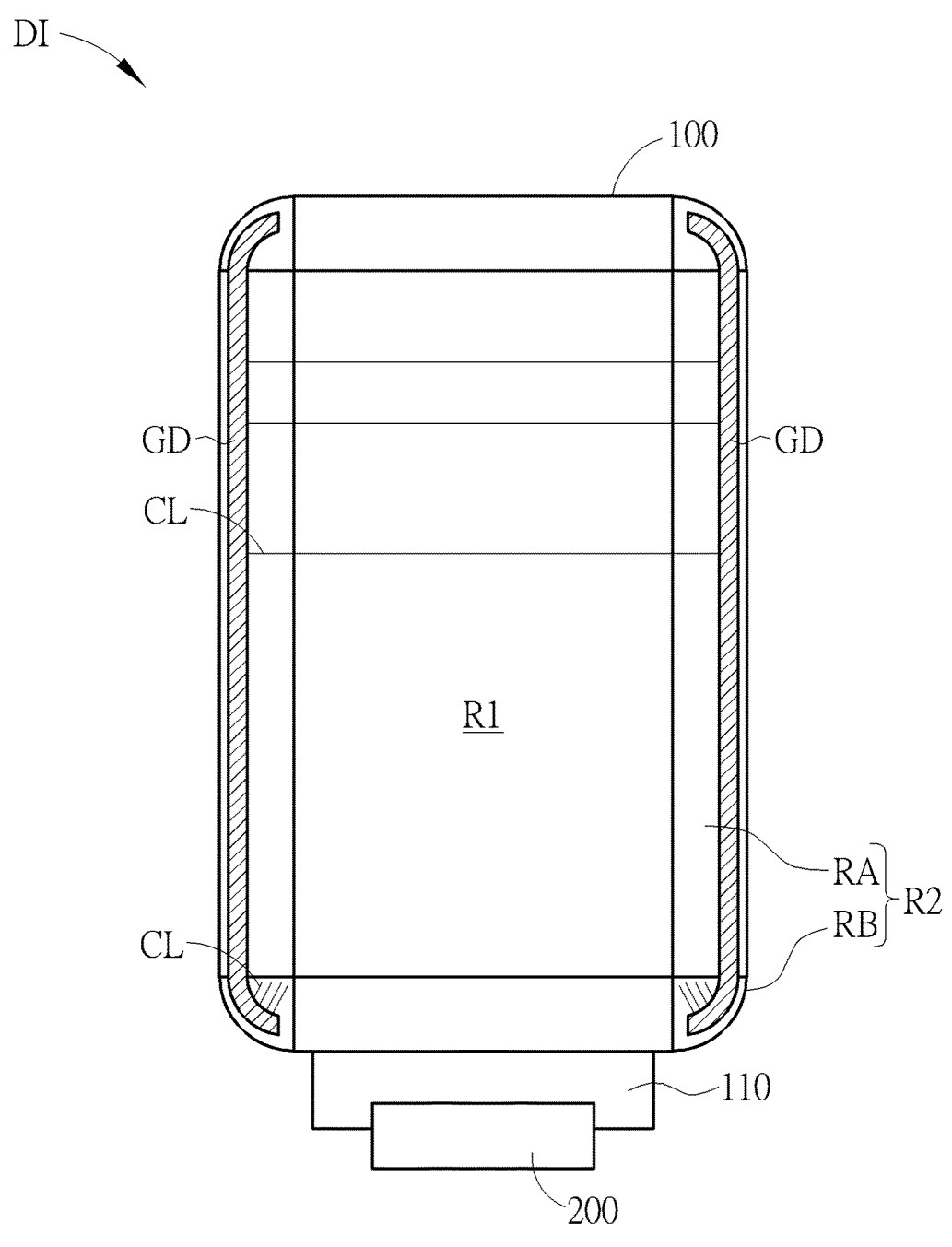
FIG. 8 is a top-view schematic diagram of the architecture of a second embodiment of a display device according the present disclosure.

Please refer to FIG. 8, which is a top-view schematic diagram of the architecture of a second embodiment of a display device according the present disclosure. According to the display device DI shown in FIG. 8, the display panel 100 may include a gate driver GD disposed in the corner area RB and at least one of the curve areas RA, and the gate driver GD is configured to provide a plurality of scan signals to the first area R1 and the second area R2. As shown in FIG. 8, the gate driver GD is disposed in the curve area RA and the corner areas RB, so that the portion of the gate driver GD located in the corner area RB may provide scan signals to the corner area RB through a short wires CL, which may reduce the signal transmission path, thereby improving the transmission efficiency or quality of the signals.

According to the embodiment shown in FIG. 7 and FIG. 8, different data signals may be provided to the first area R1, the curve areas RA and the corner areas RB, so that the visual image change rate (including brightness change, gray level change and color change) of each area is different.

Figure 9:
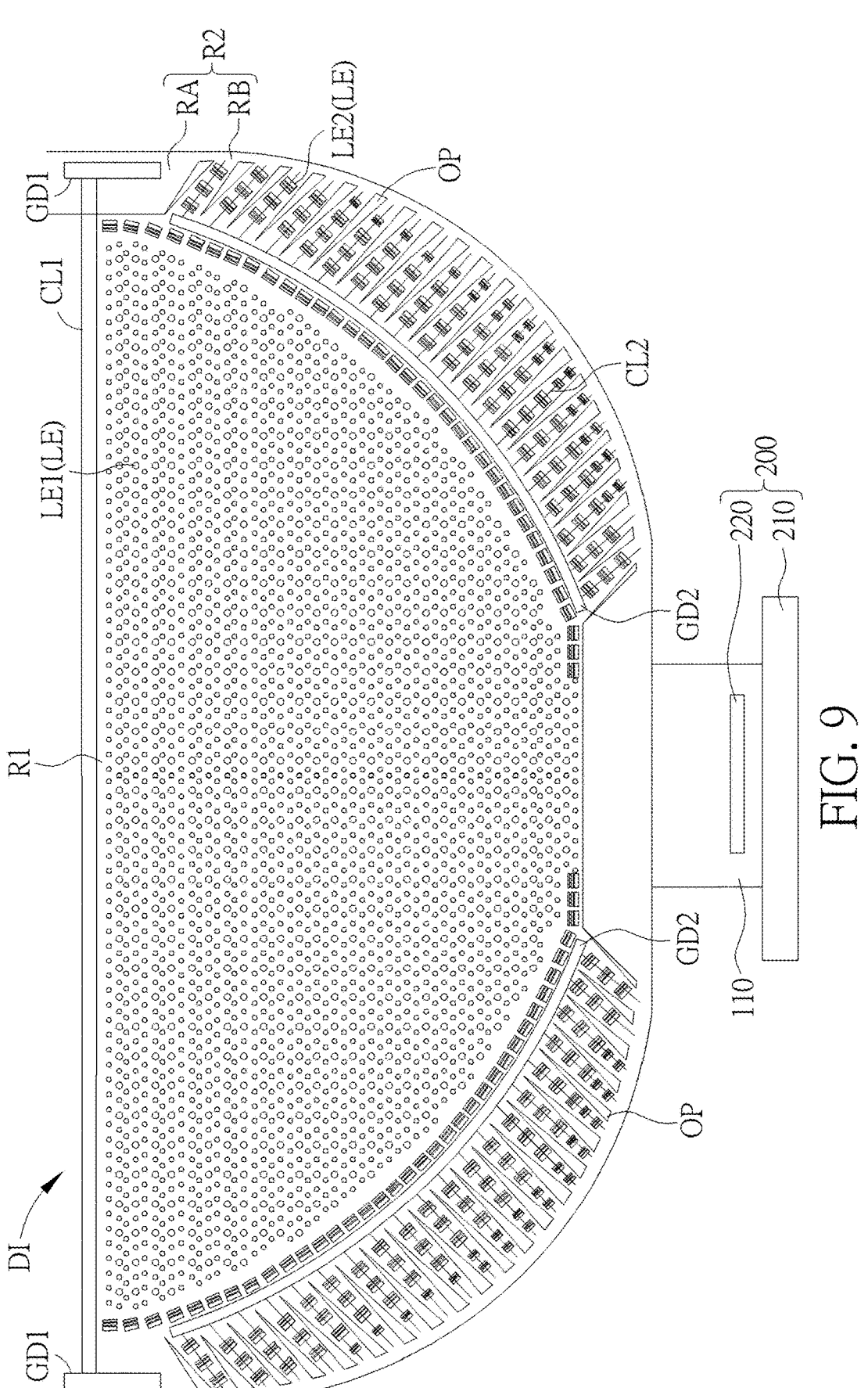
FIG. 9 is a partial top-view schematic diagram of the architecture of a third embodiment of a display device according the present disclosure.

Please refer to FIG. 9, in conjunction with FIG. 1. FIG. 9 is a partial top-view schematic diagram of the architecture of a third embodiment of a display device according the present disclosure, wherein the complete architecture of the display device DI shown in FIG. 9 may refer to FIG. 1. As shown in FIG. 9, the display panel 100 may include a first gate driver GD1 and a second gate driver GD2, the first gate driver GD1 is configured to provide a plurality of first scan signals to the first area R1, and the second gate driver GD2 is configured to provide a plurality of second scan signals to the second area R2. According to the embodiment shown in FIG. 9, the first gate driver GD1 may be disposed in at least one of the curve areas RA, and the first gate driver GD1 may provide the first scan signals to the first area R1 through a plurality of wires CL1. The second gate driver GD2 may be disposed in the corner area RB, and the second gate driver GD2 may provide the second scan signals to the corner area RB through a plurality of wires CL2. According to the wiring arrangement of the wires CL1 and the wires CL2, the first gate driver GD1 or the second gate driver GD2 may further provide the first scan signals or the second scan signals to at least one of the curve areas RA. Each of the first gate driver GD1 and the second gate driver GD2 is, for example (but not limited to), a gate driver on panel, which may be located in the peripheral area of the area that it is disposed. In some embodiments, the display panel 100 may include two first gate drivers GD1 and four second gate drivers GD2, the two first gate drivers GD1 may be respectively disposed in two curve areas RA located at two opposite sides (e.g., left and right sides) of the first area R1, and the four second gate drivers GD2 may be respectively disposed in four corner areas RB, but not limited herein.

According to the arrangement of the gate drivers and the wires shown in FIG. 9, the first gate driver GD1 and the second gate driver GD2 may respectively provide the first scan signals and the second scan signals with different driving frequencies to the corresponding first area R1, curve area RA and corner area RB, so that the driving refresh rate of the corresponding areas are different. In addition, different data signals may be provided to the first area R1, the curve areas RA and the corner areas RB, so that the visual image change rate of each area is different. In some embodiment, the first gate driver GD1 and the second gate driver GD2 may respectively provide the first scan signals and the second scan signals with the same driving frequency.

As shown in FIG. 9, the display panel 100 may include a plurality of light-emitting elements LE disposed in the first area R1, the curve areas RA and the corner areas RB. It should be noted that, in the practical structure, the light-emitting elements LE shown in FIG. 9 are disposed above the wires CL1 and the wires CL2. Three adjacent light-emitting elements LE may form a pixel. That is to say, the area of one light-emitting element LE depicted in the top view as shown in FIG. 9 may correspond to the area of one sub-pixel. In some embodiments, three adjacent light-emitting elements LE may emit red light, green light and blue light respectively. In some embodiments, the area corresponding to a blue sub-pixel may be greater than the area of a red sub-pixel and/or a green sub-pixel, but not limited herein. The light-emitting element LE is, for example, an organic light-emitting diode, a mini light-emitting diode, a micro light-emitting diode or a quantum dot light-emitting diode, but not limited herein. According to the embodiment shown in FIG. 9, the plurality of light-emitting elements LE may include a light-emitting element LE1 and a light-emitting element LE2, and the size of the light-emitting element LE2 may be greater than the size of the light-emitting element LE1. The light-emitting elements LE1 may be disposed in the first area R1, and the light-emitting elements LE2 may be disposed in the corner area RB.

Figure 10:
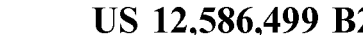
FIG. 10 is a partial top-view schematic diagram of the architecture of a fourth embodiment of a display device according the present disclosure.

Please refer to FIG. 10, which is a partial top-view schematic diagram of the architecture of a fourth embodiment of a display device according the present disclosure, wherein the complete architecture of the display device DI shown in FIG. 10 may refer to FIG. 1. According to the embodiment shown in FIG. 10, the first gate driver GD1 and the second gate driver GD2 may disposed in the first area R1, wherein the first gate driver GD1 may be disposed at an edge position near the curve area RA in the first area R1, and the second gate driver GD2 may be disposed at an edge position near the corner area RB in the first area R1. The first gate driver GD1 may provide a plurality of first scan signals to the first area R1 through the wires CL1 respectively, and the second gate driver GD2 may provide a plurality of second scan signals to the corner area RB through the wires CL2 respectively. Each of the first gate driver GD1 and the second gate driver GD2 is, for example (but not limited to), a gate driver in pixel (GIP), that is, the first gate driver GD1 and the second gate driver GD2 may be overlapped with the pixels (or the display area). It should be noted that, in the practical structure, the light-emitting elements LE shown in FIG. 10 are disposed above the first gate driver GD1, the second gate driver GD2, the wires CL1 and the wires CL2.

Figure 11:
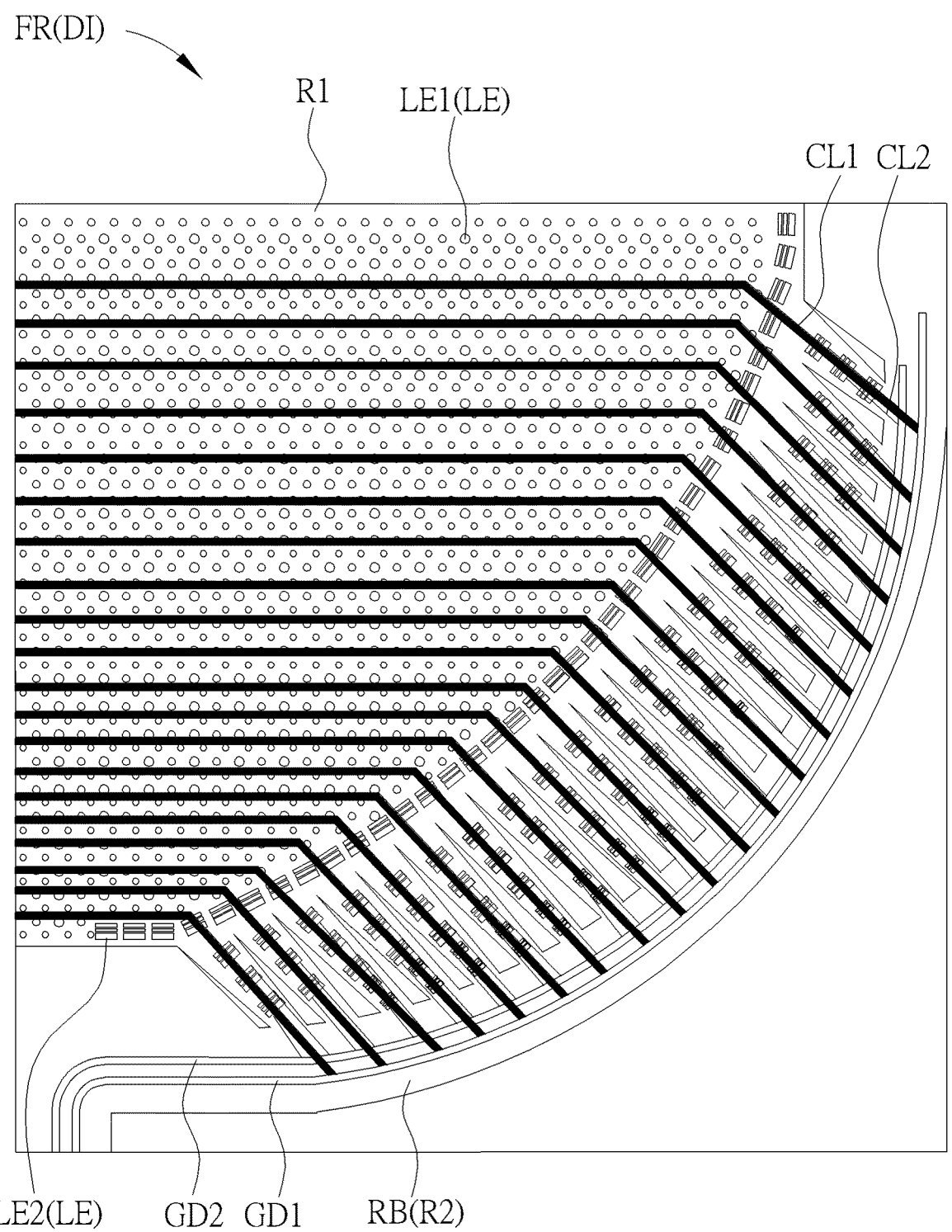
FIG. 11 is a partial top-view schematic diagram of the architecture of a fifth embodiment of a display device according the present disclosure.

Please refer to FIG. 11, which is a partial top-view schematic diagram of the architecture of a fifth embodiment of a display device according the present disclosure, wherein the complete architecture of the display device DI shown in FIG. 11 may refer to FIG. 1. For example, FIG. 11 may be a partially enlarged top view of an area FR framed by a dotted line in FIG. 1. According to the embodiment shown in FIG. 11, the first gate driver GD1 and the second gate driver GD2 may be disposed in the corner area RB, such as being disposed at the position near the arc-shaped edge in the corner area RB. Each of the first gate driver GD1 and the second gate driver GD2 is, for example (but not limited to), a gate driver on panel. The first gate driver GD1 is configured to provide the first scan signals to the first area R1 through a plurality of wires CL1 (which may be referred to as first wires in this embodiment), the second gate driver GD2 is configured to provide the second scan signals to the corner area RB through a plurality of wires CL2 (which may be referred to as second wires in this embodiment), and the wires CL1 and the wires CL2 are in different layers. That is to say, the first gate driver GD1 and the second gate driver GD2 may respectively transmit the first scan signals and the second scan signals through the wires located at different layers in the structure, wherein the first scan signals and the second scan signals may have different driving frequencies.

Figure 12:
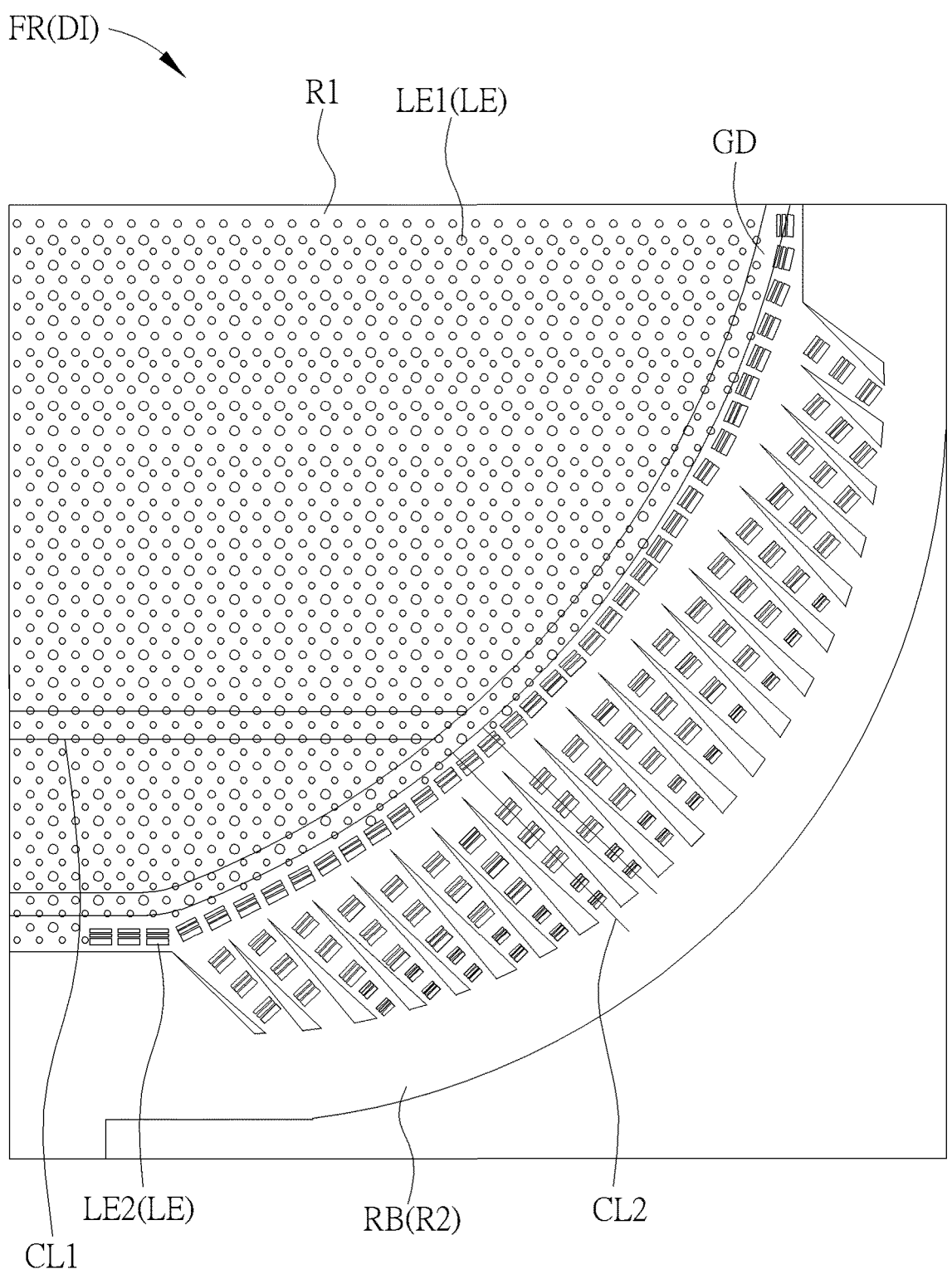
FIG. 12 is a partial top-view schematic diagram of the architecture of a sixth embodiment of a display device according the present disclosure.

Please refer to FIG. 12, which is a partial top-view schematic diagram of the architecture of a sixth embodiment of a display device according the present disclosure, wherein the complete architecture of the display device DI shown in FIG. 12 may refer to FIG. 1. For example, FIG. 12 may be a partially enlarged top view of the area FR framed by a dotted line in FIG. 1. As shown in FIG. 12, the display panel 100 may include a gate driver GD disposed at an edge position near the corner area RA in the first area R1. The gate driver GD is configured to provide signals to the first area R1 and the second area R2 in two different directions respectively. For example, the gate driver GD may provide a plurality of scan signals to the first area R1 through the wires CL1 respectively, and the gate driver GD may further provide a plurality of scan signals to the corner area RB through the wires CL2 respectively.

Figure 13:
FIG. 13 is a partial top-view schematic diagram of the architecture of a seventh embodiment of a display device according the present disclosure.

Please refer to FIG. 13, which is a partial top-view schematic diagram of the architecture of a seventh embodiment of a display device according the present disclosure, wherein the complete architecture of the display device DI shown in FIG. 13 may refer to FIG. 1. According to the embodiment shown in FIG. 13, the display panel 100 may include two first gate drivers GD1 and two second gate drivers GD2, wherein the two first gate drivers GD1 are disposed in two curve areas RA located at two opposite sides (e.g., left and right sides) of the first area R1, and the two second gate drivers GD2 are disposed in two corner areas RB located at two opposite sides (e.g., left and right sides) of the first area R1. The two first gate drivers GD1 may respectively provide a plurality of first scan signals to the first area R1 through the wires CL1, and the two second gate drivers GD2 may respectively provide a plurality of second scan signals to the corner area RB and the first area R1 through the wires CL2. Specifically, the display panel 100 may include a plurality of thin film transistors (TFTs), which are respectively electrically connected to one of the light-emitting elements LE. The above thin film transistors may be indium gallium zinc oxide (IGZO) thin film transistors. Furthermore, the second gate drivers GD2 may provide the second scan signals to the thin film transistors in the first area R1 and the corner areas RB through the wires CL2 in a bilateral driving method.

Figure 14:
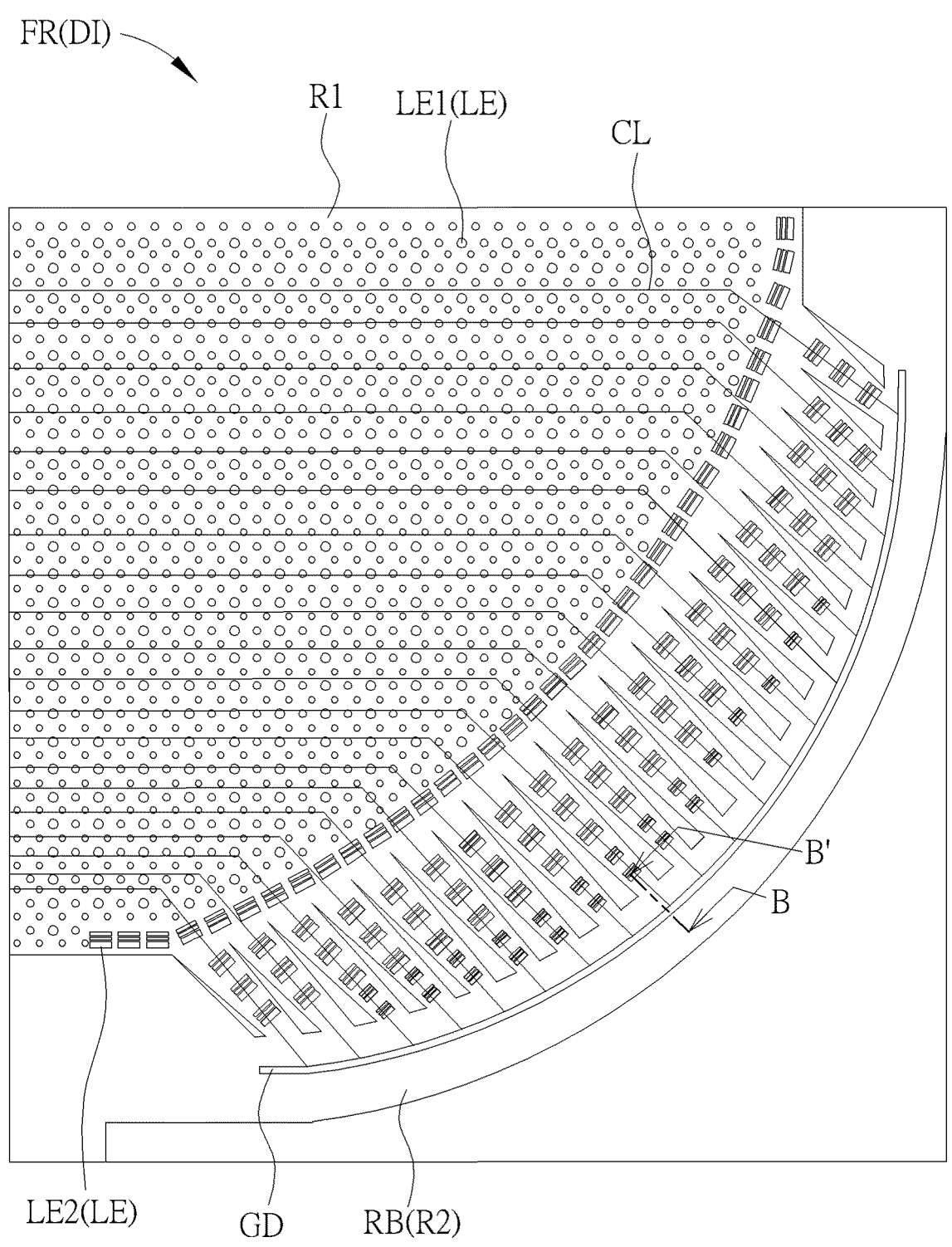
FIG. 14 is a partial top-view schematic diagram of the architecture of an eighth embodiment of a display device according the present disclosure.
Figure 15:
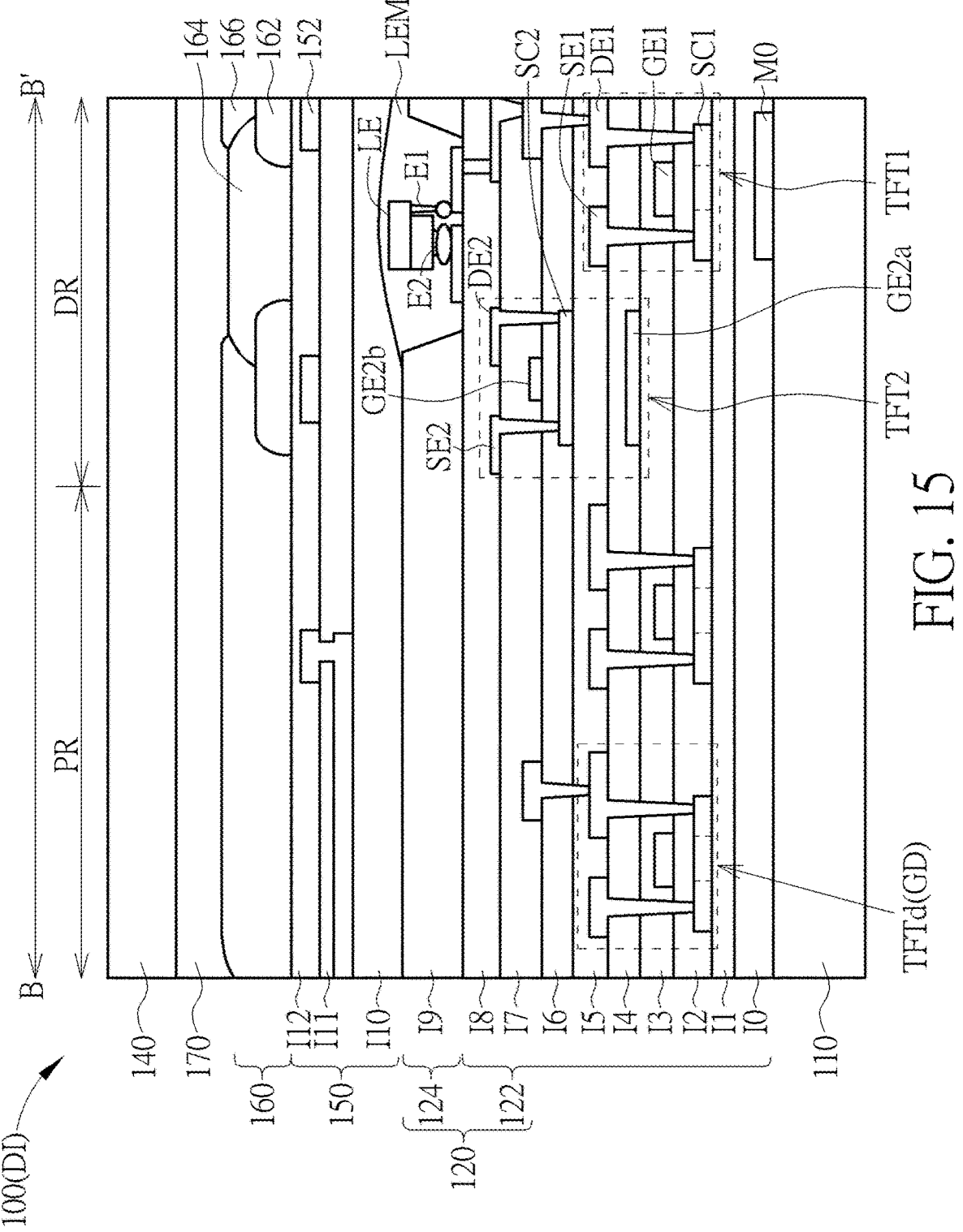
FIG. 15 is a partial cross-sectional schematic diagram of a display device according an eighth embodiment of the present disclosure.

Please refer to FIG. 14 and FIG. 15. FIG. 14 is a partial top-view schematic diagram of the architecture of an eighth embodiment of a display device according the present disclosure. FIG. 15 is a partial cross-sectional schematic diagram of a display device according an eighth embodiment of the present disclosure, wherein FIG. 15 may be a schematic sectional view along a section line B-B' of FIG. 14. According to the embodiment shown in FIG. 14 and FIG. 15, the display layer 120 of the display panel 100 may include a plurality of light-emitting elements LE, a plurality of first thin film transistors TFT1, a plurality of second thin film transistors TFT2 and a gate driver GD. The light emitting elements LE, the first thin film transistors TFT1 and the second thin film transistors TFT2 may be disposed in the display area DR of the display panel 100 (e.g., in the display areas of the first area R1 and the corner area RB). The first thin film transistor TFT1 may be electrically connected to the light-emitting element LE and serve as a driving transistor to drive the light-emitting element LE, wherein the first thin film transistor TFT1 may be a low temperature poly-silicon (LTPS) thin film transistor. The first thin film transistor TFT1 may include a gate GE1, a drain DE1, a source SE1 and a semiconductor layer SC1, and an insulating layer I2 is provided between the gate GE1 and the semiconductor layer SC1 as a gate dielectric layer. Below the first thin film transistor TFT1, a light shielding layer M0 may be further disposed on the substrate 110 of the display panel 100 to correspond to the first thin film transistor TFT1. The second thin film transistor TFT2 may serve as a switching transistor, wherein the second thin film transistor TFT2 may be an indium gallium zinc oxide thin film transistor. The second thin film transistor TFT2 may include a gate GE2a, a gate GE2*b*, a drain DE2, a source SE2 and a semiconductor layer SC2, and an insulating layer I4 and an insulating layer I6 are respectively provided between the semiconductor layer SC2 and the gate GE2*a* and the gate GE2*b* as gate dielectric layers.

The gate driver GD may be disposed in the peripheral area PR (e.g., in the peripheral area of the corner area RB) of the display panel 100, and the gate driver GD may include a plurality of thin film transistors TFTd, wherein the thin film transistor TFTd may be a low temperature poly-silicon thin film transistor and the detailed structure thereof may refer to the above first thin film transistor TFT1, which will not be redundantly described herein. The gate driver GD may provide a plurality of scan signals to the corner area RB and the first area R1 through a plurality of wires CL respectively.

The detailed structure of the display panel 100 shown in FIG. 15 will be further described below, but the present disclosure is not limited thereto. According to the embodiment shown in FIG. 15, the display panel 100 may include the substrate 110, the display layer 120, a touch layer 150, an optical structure 160, an organic layer 170 and a cover layer 140. The display layer 120 is disposed on the substrate 110 and includes a circuit layer 122 and a light-emitting layer 124. The circuit layer 122 may include the light shielding layer M0 disposed on the upper surface of the substrate 110, an insulating layer I0 disposed on the light shielding layer M0, and an insulating layer I1 (e.g., a buffer layer and the material thereof may include silicon oxide (SiOx) and/or silicon nitride (SiNx)) disposed on the insulating layer I0. The semiconductor layer SC1 is disposed on the insulating layer I1, the insulating layer I2 is disposed on the semiconductor layer SC1, the gate GE1 is disposed on the insulating layer I2, an insulating layer I3 is disposed on the gate GE1, the gate GE2*a* is disposed on the insulating layer I3, the insulating layer I4 is disposed on the gate GE2*a*, the source SE1 and the drain DE1 are disposed on the insulating layer I4 and respectively electrically connected to the semiconductor layer SC1, an insulating layer I5 is disposed on source SE1 and drain DE1, the semiconductor layer SC2 is disposed on the insulating layer I5, the insulating layer I6 is disposed on the semiconductor layer SC2, the gate GE2*b* is disposed on the insulating layer I6, an insulating layer I7 is disposed on the gate GE2*b*, the source SE2 and the drain DE2 are disposed on the insulating layer I7 and respectively electrically connected to the semiconductor layer SC2, and an insulating layer I8 is disposed on the source SE2 and the drain DE2. The light-emitting layer 124 may include an insulating layer I9 (e.g., a pixel definition layer) disposed on the insulating layer I8, a plurality of light-emitting elements LE and a encapsulating layer LEM covering each light-emitting element LE, and the insulating layer I9 may have a plurality of openings for respectively disposing the light-emitting elements LE. As shown in FIG. 15, each light-emitting element LE may include, for example, a first electrode E1 and a second electrode E2, and the first electrode E1 may be electrically connected to the drain DE1 through the metal layer(s) in the circuit layer 122, while the second electrode E2 may be electrically connected to a common electrode, but not limited herein. In some embodiments, the circuit layer 122 may further include other active elements, passive elements and/or wires.

The touch layer 150 may be disposed on the display layer 120, and the touch layer 150 may include touch elements 152, insulating layers I10 and I11 disposed between the touch elements 152 and the insulating layer I9, and an insulating layer I12 covering the touch elements 152. The touch elements 152 may be, for example (but not limited to), formed of one or more metal layers. The optical structure 160 may include a light shielding layer 162, a color filter 164 and a light shielding layer 166. The light shielding layer 162 may have a plurality of openings respectively overlapped with one of the light-emitting elements LE, and the color filter 164 is disposed in one of the openings of the light shielding layer 162. The light shielding layer 166 is disposed on the light shielding layer 162, and the light shielding layer 166 may have a plurality of openings overlapped with one of the openings of the light shielding layer 162. The organic layer 170 is disposed on the light shielding layer 166 and the color filter 164, which may serve as a planarization layer to fill in the irregular terrain below. The cover layer 140 may be attached to the organic layer 170 or directly formed on the organic layer 170.

Figure 16:
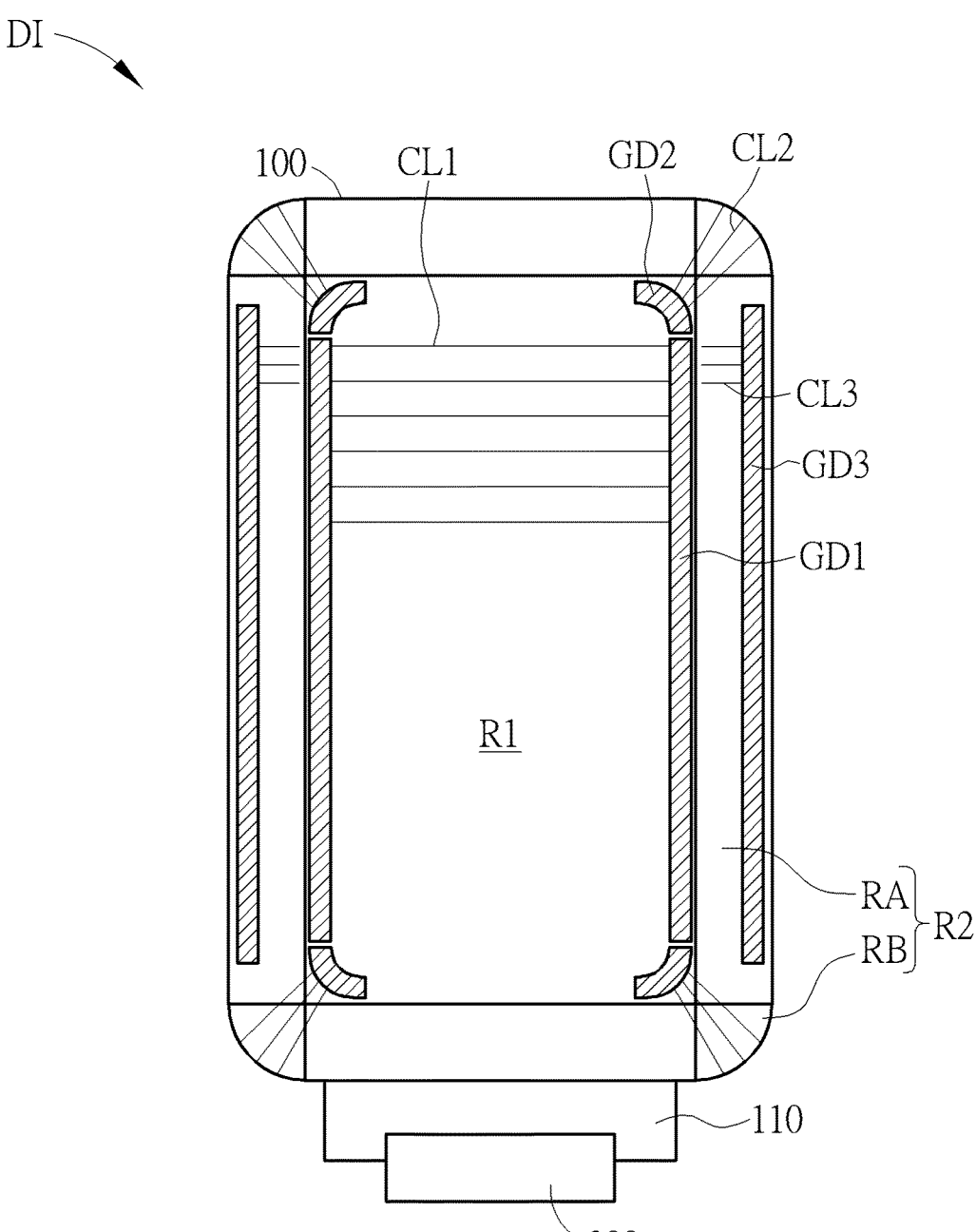
FIG. 16 is a top-view schematic diagram of the architecture of a ninth embodiment of a display device according the present disclosure.

Please refer to FIG. 16, which is a top-view schematic diagram of the architecture of a ninth embodiment of a display device according the present disclosure. According to the display device DI shown in FIG. 16, the display panel 100 may include a first gate driver GD1, a second gate driver GD2 and a third gate driver GD3. The first gate driver GD1 is configured to provide a plurality of first scan signals to the first area R1, the second gate driver GD2 is configured to provide a plurality of second scan signals to the corner area RB, and the third gate driver GD3 is configured to provide a plurality of third scan signals to the curve area RA. As show in FIG. 16, the first gate driver GD1 and the second gate driver GD2 may be disposed in the first area R1, wherein the first gate driver GD1 may be disposed at the edge position near the curve area RA in the first area R1, and the second gate driver GD2 may be disposed at the edge position near the corner area RB in the first area R1. The third gate driver GD3 may be disposed in the peripheral area of the curve area RA. The first gate driver GD1 may provide the first scan signals to the first area R1 through a plurality of wires CL1, the second gate driver GD2 may provide the second scan signals to the corner area RB through a plurality of wires CL2, and the third gate driver GD3 may provide the third scan signals to the curve area RA through a plurality of wires CL3. Each of the first gate driver GD1 and the second gate driver GD2 is, for example (but not limited to), a gate driver in pixel. The third gate driver GD3 is, for example (but not limited to), a gate driver on panel. In some embodiments, the display panel 100 may include two first gate drivers GD1, four second gate drivers GD2, and two third gate drivers GD3. The two first gate drivers GD1 may be respectively disposed in the edge positions in the first area R1 near the curve areas RA at two opposite sides (e.g., left and right sides) of the first area R1, the four second gate drivers GD2 may be respectively disposed in the edge positions near the four corner areas RB in the first area R1, and the two third gate drivers GD3 may be respectively disposed in the two curve areas RA located at two opposite sides (e.g., left and right sides) of the first area R1, but note limited herein.

According to the arrangement of the gate drivers and the wires shown in FIG. 16, the first gate driver GD1, the second gate driver GD2 and the third gate driver GD3 may respectively provide the first scan signals, the second scan signals and the third scan signals with different driving frequencies to the corresponding first area R1, corner area RB and curve area RA, so that the driving refresh rate of the corresponding areas are different. In addition, different data signals may be provided to the first area R1, the curve areas RA and the corner areas RB, so that the visual image change rate of each area is different.

From the above description, according to the display devices of the embodiments of the present disclosure, the first area, the curve area and the corner area of the display panel may operate in a corresponding operation mode based on a condition of use of the display device, so that the effect of power saving may be achieved, and various kinds of divisional display statuses may satisfy different requirements of use. Furthermore, through the various arrangement of the gate drivers and the wires, different data signals and/or scan signals with different driving frequencies may be provided to the first area, the curve area and the corner area respectively, so that each area may have different display change rates.

Those skilled in the art will readily observe that numerous modifications and alterations of the device and method may be made while retaining the teachings of the disclosure. Accordingly, the above disclosure should be construed as limited only by the metes and bounds of the appended claims.

What is claimed is:

1. A display device, capable of operating in a plurality of conditions of use, comprising:
   a display panel having a first area and a second area surrounding the first area, wherein the second area has a plurality of curve areas and a corner area connecting two of the curve areas, wherein the display panel comprises:
      a first gate driver configured to provide a plurality of first scan signals to the first area; and
      a second gate driver configured to provide a plurality of second scan signals to the second area, wherein the first gate driver and the second gate driver are disposed in the corner area,
      wherein the first gate driver is configured to provide the first scan signals to the first area through a plurality of first wires, the second gate driver is configured to provide the second scan signals to the corner area through a plurality of second wires, and the first wires and the second wires are in different layers; and
   a processor electrically connected to the display panel, wherein the processor is configured to:

based on one of the conditions of use, determine operation modes corresponding to the first area, the curve areas and the corner area; and
      control the first area, the curve areas and the corner area to operate in the determined operation modes respectively.

2. The display device according to claim 1, wherein the conditions of use comprises a first condition of use, based on the first condition of use, the first area is operated in an off-mode or a display mode, and the curve areas and the corner area are operated in the display mode to indicate completeness of a task.

3. The display device according to claim 2, wherein the task is to charge a battery of the display device.

4. The display device according to claim 2, wherein the task is to sense a physiological status of a user, and the physiological status is one of heart rate, blood pressure and blood oxygen level.

5. The display device according to claim 2, wherein in the first condition of use, a refresh rate of the curve areas is greater than a refresh rate of the first area.

6. The display device according to claim 2, wherein when the task is complete, the curve areas and the corner area show an image surrounding the first area.

7. The display device according to claim 1, wherein the conditions of use comprises a second condition of use, based on the second condition of use, the first area, the curve areas and the corner area are operated in a display mode to show at least one image.

8. The display device according to claim 7, wherein in the second condition of use, a refresh rate of the curve areas is equal to a refresh rate of the first area.

9. The display device according to claim 1, wherein the conditions of use comprises a third condition of use, based on the third condition of use, the curve areas and the corner area are operated in an off-mode, and the first area is operated in a display mode to show a context.

10. The display device according to claim 9, wherein in the third condition of use, a refresh rate of the first area is greater than a refresh rate of the curve areas.

* * * * *